United States Patent
Hale

(10) Patent No.: US 10,464,689 B2
(45) Date of Patent: Nov. 5, 2019

(54) DIAGNOSTIC METHOD, SYSTEM AND DEVICE FOR A ROTORCRAFT DRIVE SYSTEM

(71) Applicant: Bell Helicopter Textron Inc., Fort Worth, TX (US)

(72) Inventor: Rodney Keith Hale, Joshua, TX (US)

(73) Assignee: Bell Helicopter Textron Inc., Fort Worth, TX (US)

( * ) Notice: Subject to any disclaimer, the term of this patent is extended or adjusted under 35 U.S.C. 154(b) by 114 days.

(21) Appl. No.: 15/677,885

(22) Filed: Aug. 15, 2017

(65) Prior Publication Data

US 2018/0162548 A1  Jun. 14, 2018

Related U.S. Application Data

(60) Provisional application No. 62/376,121, filed on Aug. 17, 2016.

(51) Int. Cl.
*B64D 45/00* (2006.01)
*G01N 29/46* (2006.01)
(Continued)

(52) U.S. Cl.
CPC ............. *B64D 45/00* (2013.01); *B64F 5/60* (2017.01); *G01N 29/04* (2013.01); *G01N 29/14* (2013.01);
(Continued)

(58) Field of Classification Search
CPC ........ G01N 29/46; G01N 29/14; G01N 29/04; B64D 45/00; B64F 5/60; G07C 5/0808;
(Continued)

(56) References Cited

U.S. PATENT DOCUMENTS 7,224,807 B2  5/2007  Welsh et al.
7,930,111 B2  4/2011  Luo et al.
(Continued)

FOREIGN PATENT DOCUMENTS

CN  102426102 B  7/2013
EP  0889313 A2  1/1999
(Continued)

OTHER PUBLICATIONS

Examination Report, dated Sep. 7, 2018, by the EPO, re EP Patent Application No. 17186532.2.
(Continued)

*Primary Examiner* — Helen C Kwok
(74) *Attorney, Agent, or Firm* — Timmer Law Group, PLLC

(57) ABSTRACT

A method, system, and device for diagnosing an anomaly of a monitored component in a drive train, the method including: obtaining original data based on samples of a tachometer signal; processing the original data to obtain rotational information; processing the original data to produce a sine spectrum; determining complex magnitudes of the sine spectrum; removing dominate torsional mode residuals from the complex magnitudes of the sine spectrum to produce a frequency spectrum; and determining a condition indicator from the frequency spectrum.

17 Claims, 12 Drawing Sheets

(51) Int. Cl.
*G07C 5/00* (2006.01)
*G01N 29/04* (2006.01)
*G01N 29/14* (2006.01)
*B64F 5/60* (2017.01)
*G07C 5/08* (2006.01)
*B64C 27/12* (2006.01)

(52) U.S. Cl.
CPC ............ *G01N 29/46* (2013.01); *G07C 5/002* (2013.01); *G07C 5/085* (2013.01); *G07C 5/0808* (2013.01); *B64C 27/12* (2013.01); *B64D 2045/0085* (2013.01)

(58) Field of Classification Search
CPC .. G07C 5/085; G01M 13/028; G01M 13/021; G01M 13/04; G01M 13/02
See application file for complete search history.

(56) References Cited

U.S. PATENT DOCUMENTS

| | | | |
|---|---|---|---|
| 8,131,420 | B2 | 3/2012 | Lynch et al. |
| 8,442,778 | B2 | 5/2013 | Bechhoefer et al. |
| 8,930,166 | B1 | 1/2015 | Das et al. |
| 9,145,946 | B2 | 9/2015 | Heverly, II et al. |
| 9,202,098 | B2 | 12/2015 | Lewis et al. |
| 9,308,822 | B2 | 4/2016 | Matsuda |
| 9,404,891 | B2 | 8/2016 | Lih et al. |
| 9,482,647 | B2 | 11/2016 | Isom et al. |
| 9,561,863 | B2 | 2/2017 | Conrad |
| 9,616,387 | B2 | 4/2017 | Eager |
| 9,645,046 | B2 * | 5/2017 | Zhang ................... G01M 13/00 |
| 9,712,936 | B2 | 7/2017 | Peters |
| 10,380,810 | B2 | 8/2019 | Hale |
| 2003/0028332 | A1 | 2/2003 | DiMaggio et al. |
| 2013/0013231 | A1 | 1/2013 | Banerjee et al. |
| 2013/0116937 | A1 * | 5/2013 | Calhoun ............. G01M 13/028 702/35 |
| 2014/0355726 | A1 | 12/2014 | Elenes et al. |
| 2015/0088435 | A1 * | 3/2015 | Isom ................... G01M 13/021 702/35 |
| 2015/0330867 | A1 * | 11/2015 | Potts ................... G01M 13/028 73/593 |
| 2016/0033580 | A1 * | 2/2016 | Qiao ..................... G01R 31/343 324/765.01 |
| 2016/0195390 | A1 | 7/2016 | Nissen et al. |
| 2016/0304192 | A1 | 10/2016 | Hale et al. |
| 2017/0011560 | A1 | 1/2017 | Sheldon et al. |
| 2017/0088257 | A1 | 3/2017 | Heverly, II et al. |
| 2017/0089805 | A1 | 3/2017 | Sheldon et al. |
| 2017/0336430 | A1 * | 11/2017 | Winslow ............... G01H 1/006 |
| 2018/0053358 | A1 | 2/2018 | Hale |
| 2018/0053359 | A1 | 2/2018 | Hale |
| 2018/0165897 | A1 | 6/2018 | Hale |

FOREIGN PATENT DOCUMENTS

| | | |
|---|---|---|
| EP | 1612458 A2 | 1/2006 |
| EP | 2221732 A1 | 8/2010 |
| EP | 2559988 A2 | 2/2013 |
| EP | 3284668 A1 | 2/2018 |
| EP | 3284669 A1 | 2/2018 |
| EP | 3284670 A1 | 2/2018 |
| EP | 3284671 A1 | 2/2018 |
| EP | 3284670 B1 | 3/2019 |
| EP | 3284671 B1 | 3/2019 |
| WO | 2004059399 A1 | 7/2004 |
| WO | 2016099645 A1 | 6/2016 |

OTHER PUBLICATIONS

Examination Report, dated Sep. 10, 2018, by the EPO, re EP Patent Application No. 17186531.4.
Communication under Rule 71(3) EPC—Intention to Grant, dated Sep. 25, 2018, re EP Patent Application No. 17186730.2.
Communication under Rule 71(3) EPC—Intention to Grant, dated Sep. 28, 2018, re EP Patent Application No. 17186726.0.
Examination Report, dated Feb. 12, 2018, by the EPO, re EP Application No. 17186726.0.
European Search Report, dated Jan. 24, 2018, by the EPO, regarding EP Application No. 17186531.4.
European Search Report, dated Jan. 24, 2018, by the EPO, regarding EP Application No. 17186532.2.
European Search Report, dated Jan. 24, 2018, by the EPO, regarding EP Application No. 17186726.0.
European Search Report, dated Jan. 24, 2018, by the EPO, regarding EP Application No. 17186730.2.
Samuel et al.; A review of vibration-based techniques for helicopter transmission diagnostics; Journal of Sound and Vibration 282; pp. 475-508; Apr. 6, 2005.
Examination Report, dated Feb. 12, 2018, by the EPO, regarding EP Application No. 17186531.4.
Examination Report, dated Feb. 12, 2018, by the EPO, regarding EP Application No. 17186532.2.
Examination Report, dated Feb. 12, 2018, by the EPO, regarding EP Application No. 17186730.2.
Sharma, et al.; A review of gear fault diagnosis using various condition indicators; Procedia Engineering 144 (2016) 253-263.
Office Action, dated Jan. 10, 2019, by the USPTO, re U.S. Appl. No. 15/677,962.
Decision to Grant, dated Feb. 7, 2019, by the EPO, re EP Patent Application No. 17186726.0.
Decision to Grant, dated Feb. 14, 2019, by the EPO, re EP Patent Application No. 17186730.2.
Irvine; Power Spectral Density Units [$G^2$ / Hz]; Mar. 15, 2007.
Huang et al; The empirical mode decomposition and the Hilbert spectrum for nonlinear and non-stationary time series analysis; Jun. 3, 1996; Proc. R. Soc. Lond. A (1998) 454, 903-995.
EP Communication under Rule 71(3) EPC, dated Apr. 4, 2019, by the EPO, re EP Patent App No. 17186531.4.
EP Communication under Rule 71(3) EPC, dated Apr. 18, 2019, by the EPO, re EP Patent App No. 17186532.2.
Office Action-Restriction, dated May 16, 2019, by the USPTO, re U.S. Appl. No. 15/677,786.
Notice of Allowance, dated Jul. 25, 2019, by the USPTO, re U.S. Appl. No. 15/677,962.

* cited by examiner

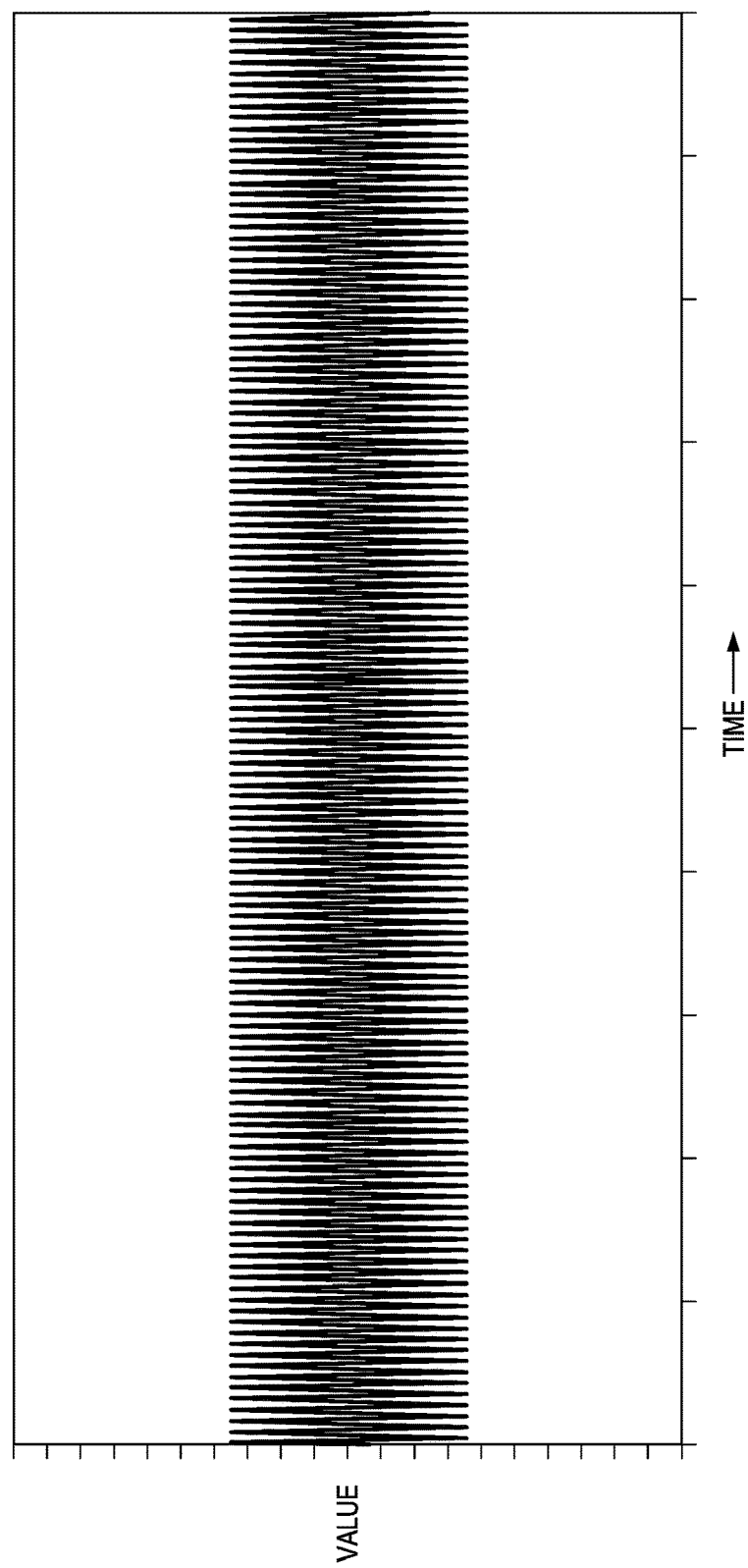

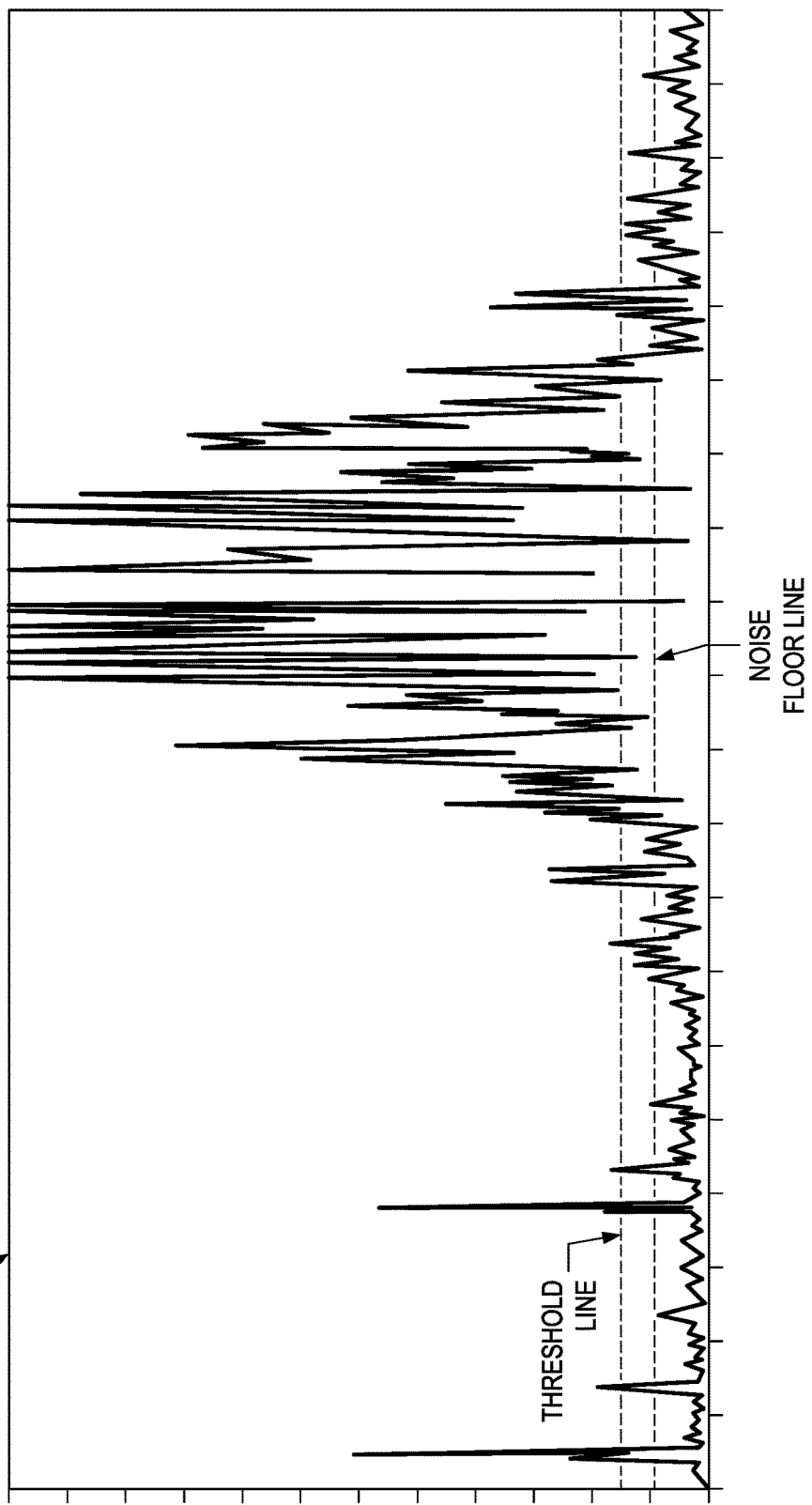

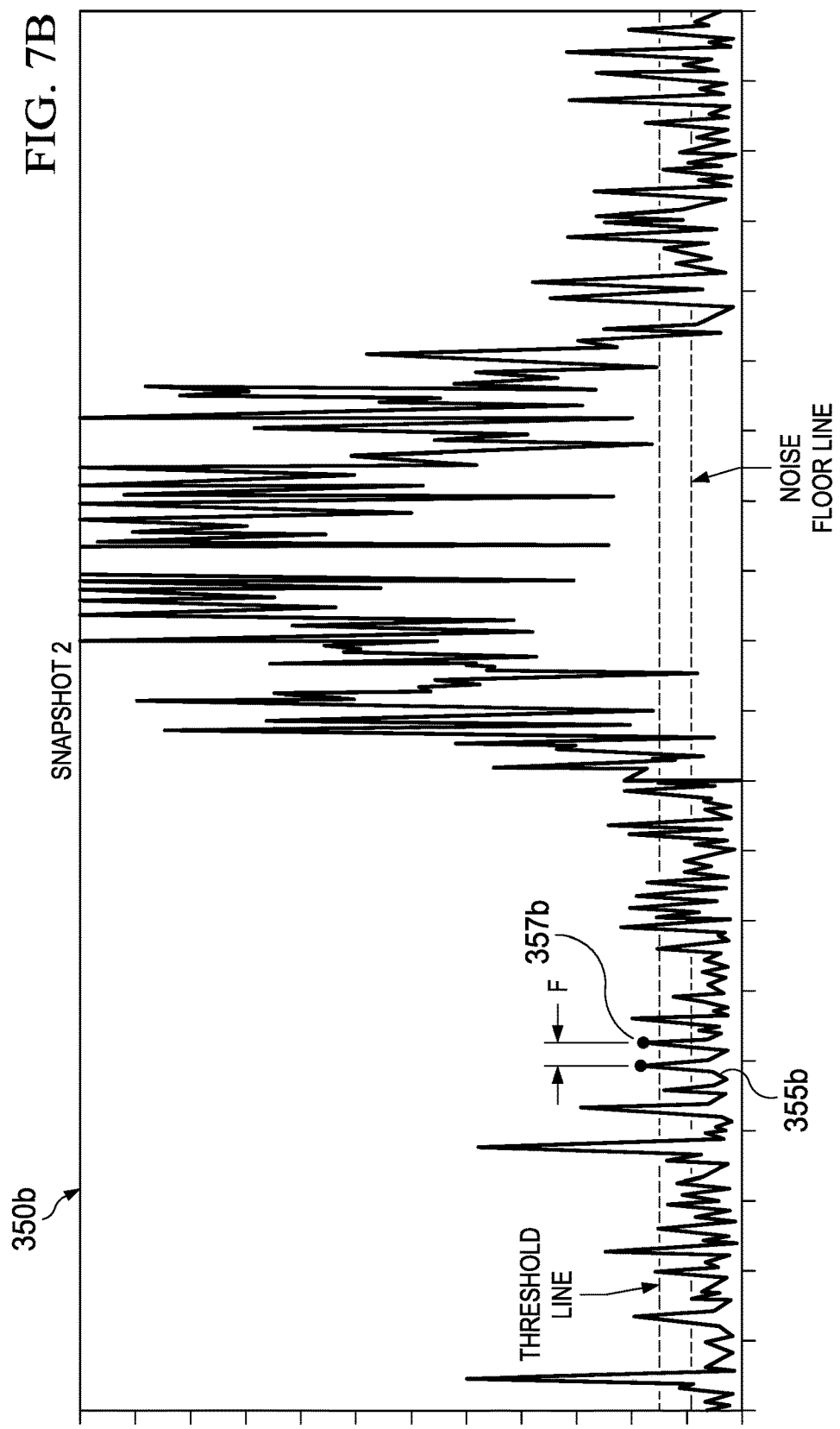

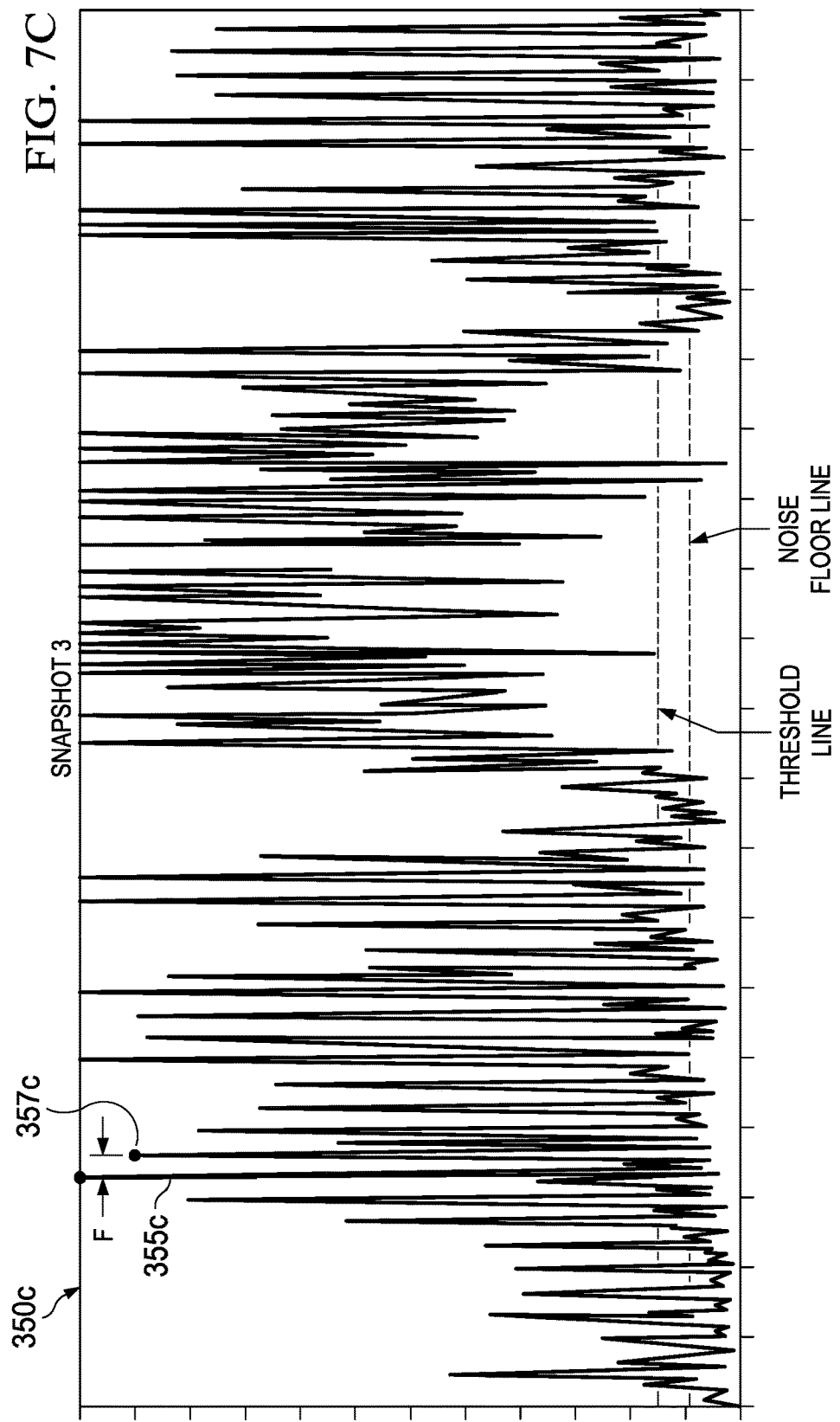

ated information; process the original data to produce a sine spectrum; determine complex magnitudes of the sine spectrum; remove dominate torsional mode residuals from the complex magnitudes of the sine spectrum to produce a frequency spectrum; and determine a condition indicator from the frequency spectrum.

DIAGNOSTIC METHOD, SYSTEM AND DEVICE FOR A ROTORCRAFT DRIVE SYSTEM

CROSS-REFERENCE TO RELATED APPLICATION

This application claims priority to U.S. Patent Application No. 62/376,121, filed Aug. 17, 2016, which is incorporated herein by reference in its entirety.

BACKGROUND

Technical Field

The present disclosure relates to a method, system, and device for diagnosing an anomaly in an aircraft drive system.

Description of Related Art

An aircraft, such as a rotorcraft or tiltrotor aircraft, may include one or more rotor systems. One example of a rotor system is a main rotor system. The main rotor system may generate aerodynamic lift to support the weight of the rotorcraft in flight and thrust to counteract aerodynamic drag and move the rotorcraft in forward flight. Another example of a rotorcraft rotor system is a tail rotor system. The tail rotor system may generate thrust in the same direction as the main rotor system's rotation to counter the torque effect created by the main rotor system. A rotor system may include a gearbox that transmits energy from a power source to the rotor blade.

The rotor and drive system are conventionally monitored using traditional time synchronous methods that receive data from at least one accelerometer as well as a tachometer. The two different sensors are typically synchronized in a precise manner that is complicated and requires precise timing and very low noise in the tachometer signal. The complexity of the traditional time synchronous methods increases cost and introduces additional potential failure modes. Failures can be difficult to diagnose due to the interplay between the two sensors.

There is a need for an improved diagnostic system, method, and device for a drive system.

SUMMARY

In a first aspect, there is a method of diagnosing an anomaly of a monitored component in a drive train, the method including: obtaining, by a device configured to diagnose an anomaly, original data based on samples of a tachometer signal; processing, by the device configured to diagnose an anomaly, the original data to obtain rotational information; processing, by the device configured to diagnose an anomaly, the original data to produce a sine spectrum; determining, by the device configured to diagnose an anomaly, complex magnitudes of the sine spectrum; removing, by the device configured to diagnose an anomaly, dominate torsional mode residuals from the complex magnitudes of the sine spectrum to produce a frequency spectrum; and determining, by the device configured to diagnose an anomaly, a condition indicator from the frequency spectrum.

In an embodiment, the step of processing to produce a sine spectrum comprises performing a discrete Fourier transform (DFT).

In another embodiment, the step of removing dominate torsional mode residuals includes monitoring torsional vibrations in a gearbox in a drivetrain of a rotorcraft; and identifying the dominate torsional mode residuals of the gearbox.

In one embodiment, the step of determining a condition indicator includes the following steps: (a) determining a threshold of the frequency spectrum; (b) determining a noise floor of the frequency spectrum; (c) detecting peaks over the threshold; and (d) summing the magnitudes of the peaks over the threshold that are separated in frequency by the rotating speed of the monitored component to determine a condition indicator.

In an embodiment, the method includes determining a plurality of condition indicators.

In still another embodiment, the method includes based upon the plurality of condition indicators, determining an unhealthy condition of the plurality of condition indicators.

In yet another embodiment, the method includes identifying an unhealthy component.

In an embodiment, the method includes adjusting at least one of the operation and maintenance of the unhealthy component.

In one embodiment, the device configured to diagnose an anomaly further includes a display; wherein the device provides a real-time indication of an anomaly in the monitored component.

In an embodiment, the method includes storing a history, by the device configured to diagnose an anomaly, of original data; wherein the history being stored before the diagnostic operation for the component is performed.

In a second aspect, there is a device configured to diagnose an anomaly of a monitored component in a drive train, the device including: a memory configured to store original data of a tachometer signal; one or more processors in communication with the memory, the one or more processors being configured to: obtain original data based on samples of a tachometer signal; process the original data to obtain rotational information; process the original data to produce a sine spectrum; determine complex magnitudes of the sine spectrum; remove dominate torsional mode residuals from the complex magnitudes of the sine spectrum to produce a frequency spectrum; and determine a condition indicator from the frequency spectrum.

In an embodiment, the processors are configured to determine a plurality of condition indicators.

In one embodiment, the processors are configured to, based upon the plurality of condition indicators, determine an unhealthy condition of the plurality of condition indicators; and identify an unhealthy component.

In yet another embodiment, the processors are configured to adjust at least one of the operation and maintenance of the unhealthy component.

In another embodiment, the device includes a display; wherein the device provides a real-time indication of an anomaly in the monitored component.

In an embodiment, the original data is stored before the diagnostic operation for the component is performed.

In a third aspect, there is a system for diagnosing an anomaly of a monitored component in a drive train, the system including a rotorcraft comprising a body, a power train coupled to the body and comprising a power source and a drive train coupled to the power source; a tachometer coupled to the drive train; and a diagnostic device associated with the vibration sensor system, the diagnostic device operable to: obtain original data based on samples of a tachometer signal; process the original data to obtain rotational information; process the original data to produce a sine spectrum; determine complex magnitudes of the sine spectrum; remove dominate torsional mode residuals from the complex magnitudes of the sine spectrum to produce a frequency spectrum; and determine a condition indicator from the frequency spectrum.

In a fourth aspect, there is a non-transitory computer-readable storage medium encoded with instructions that, when executed, cause one or more processors of a computing device to diagnose an anomaly of a monitored component in a drive train to: obtain original data based on samples of a tachometer signal; process the original data to obtain rotational information; process the original data to produce a sine spectrum; determine complex magnitudes of the sine spectrum; remove dominate torsional mode residuals from the complex magnitudes of the sine spectrum to produce a frequency spectrum; and determine a condition indicator from the frequency spectrum.

Other aspects, features, and advantages will become apparent from the following detailed description when taken in conjunction with the accompanying drawings, which are a part of this disclosure and which illustrate, by way of example, principles of the inventions disclosed.

DESCRIPTION OF THE DRAWINGS

The novel features believed characteristic of the embodiments of the present disclosure are set forth in the appended claims. However, the embodiments themselves, as well as a preferred mode of use, and further objectives and advantages thereof, will best be understood by reference to the following detailed description when read in conjunction with the accompanying drawings, wherein:

FIG. 3C is a graph showing original data from a tachometer, according to an illustrative embodiment;

FIGS. 7A-7C are graphs illustrating three snapshots in time of frequency spectrums of a component degrading, according to an illustrative embodiment;

DESCRIPTION OF THE PREFERRED EMBODIMENT

Illustrative embodiments of a method, system, and device for diagnosing an anomaly in an aircraft drive system are described below. In the interest of clarity, all features of an actual implementation may not be described in this specification. It will, of course, be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction.

Figure 1:
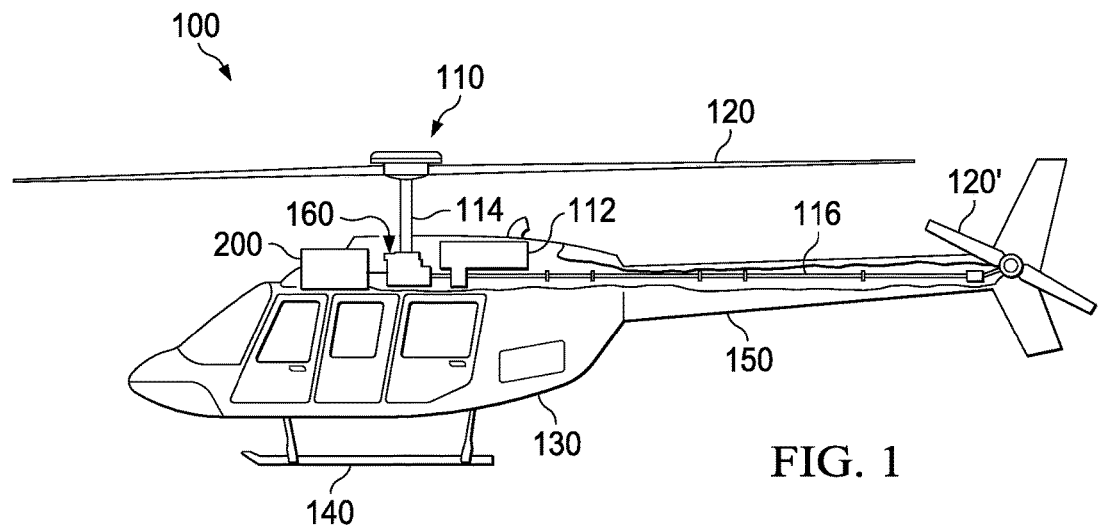
FIG. 1 is a side view of a rotorcraft, according to an example embodiment.

Referring to FIG. 1 in the drawings, a rotorcraft 100 is illustrated. Rotorcraft 100 can include drive train system 110, main rotor blades 120, tail rotor blades 120', a fuselage 130, a landing gear 140, and a tail member 150. Drive train system 110 may rotate blades 120 and/or blades 120'. Drive train system 110 and blades 120' may collectively provide thrust in the same direction as the rotation of blades 120 so as to counter the torque effect created by blades 120.

Fuselage 130 represents the body of rotorcraft 100 and may be coupled to drive train system 110 such that drive train system 110 and blades 120 move fuselage 130 through the air. Landing gear 140 supports rotorcraft 100 when rotorcraft 100 is landing and/or when rotorcraft 100 is at rest on the ground. The tail member 150 represents the tail section of the aircraft and features blades 120'.

In the example shown in FIG. 1, drive train system 110 includes an engine 112, a gearbox 160, a main rotor mast 114, and a tail rotor drive shaft 116. Engine 112 supplies torque to the main rotor mast 114 via gearbox 160 for rotating of blades 120. Engine 112 also supplies torque to tail rotor drive shaft 116 for rotating of blades 120'. In the example of FIG. 1, gearbox 160 is a main rotor transmission system. Teachings of certain embodiments recognize, however, that drive train system 110 may include more or different gearboxes than gearbox 160 shown in FIGS. 1 and 2A-2B. Drive train system 110 may include a control system for selectively controlling the pitch of each blade 120 in order to selectively control direction, thrust, and lift of rotorcraft 100. Gears, bearings, main rotor mast, and tail rotor drive shaft, and other mechanical components or systems of drive train 110 rotate during operation.

Rotorcraft 100 further comprises a diagnostic system 200 for detecting an anomaly of a monitored component configured to identify and alert an operator, technician, or manufacturer to vibratory anomalies that may reflect a malfunctioning gear, bearing or other drive system related component. It should be appreciated that teachings from rotorcraft 100 may apply to aircraft other than rotor, such as airplanes, tiltrotor, hovercraft, unmanned aircraft, to name a few examples, and may apply to other industries including, but not limited to, automotive, ships, and industrial applications involving fixed equipment with rotational elements. The embodiments herein are illustrated with regard to a drive train for a main rotor assembly on a rotorcraft; however, it should be appreciated that the embodiments may be adaptable to a tail rotor assembly.

Figure 2A:
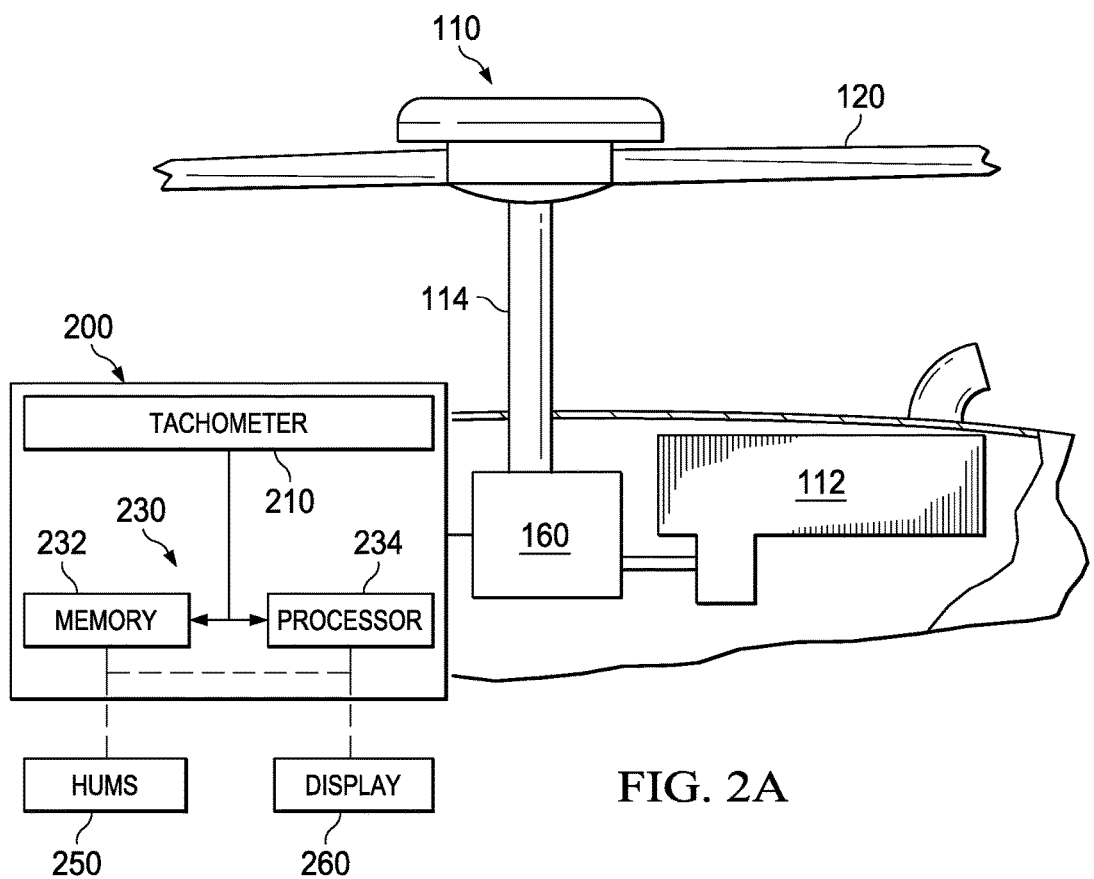
FIGS. 2A-2B shows exemplary diagnostic systems with a drive train system for a rotorcraft.
Figure 2B:
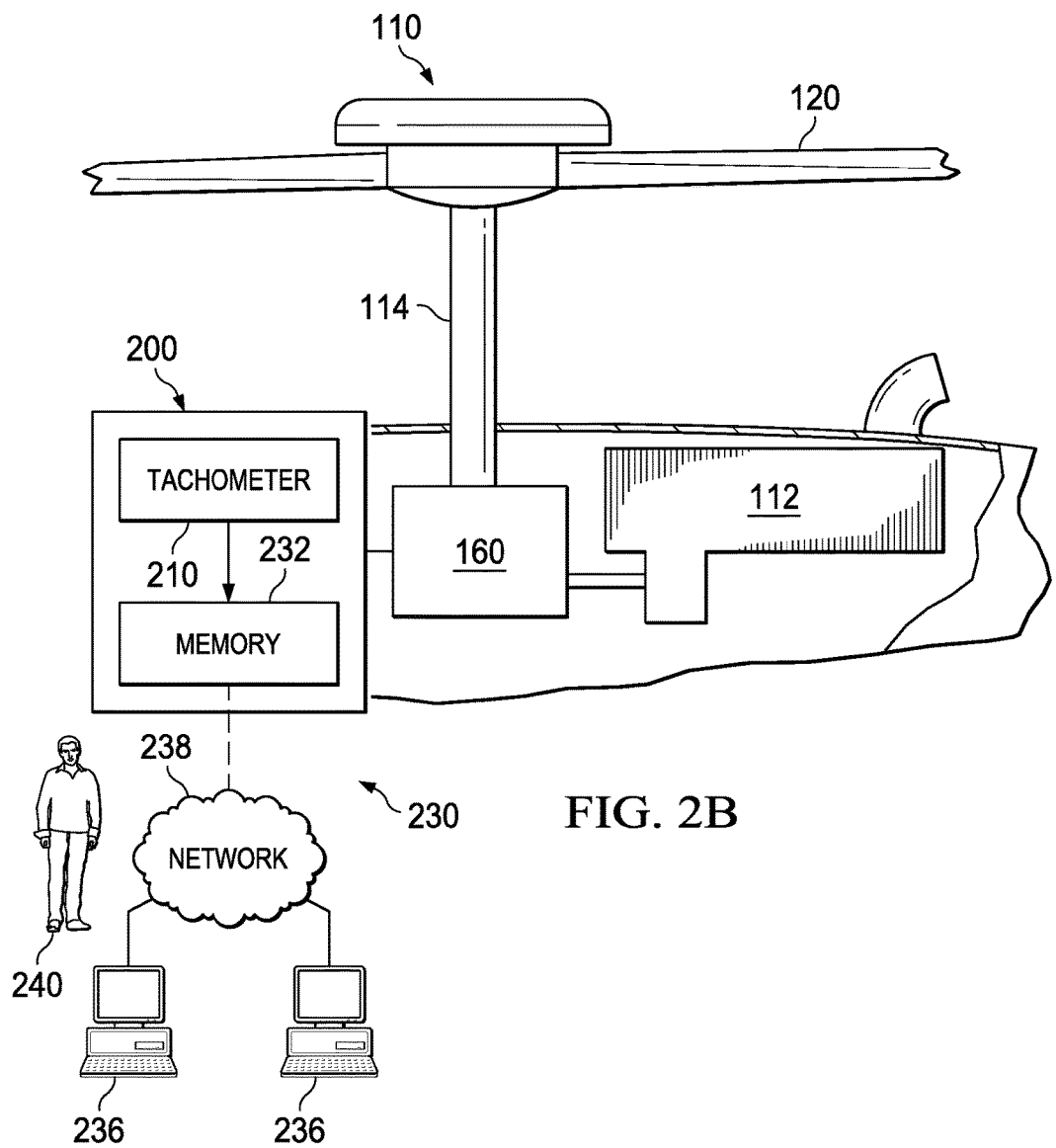

Diagnostic system 200, as shown in FIGS. 2A-2B, includes a tachometer 210 coupled to the drive train 110 and a diagnostic device 230, as shown in FIGS. 2A-2B. The diagnostic device 230 can represent any form of computing device capable of implementing the techniques described in this disclosure, including a handset (or cellular phone), a tablet computer, a smart phone, or a desktop computer. Diagnostic device 230 is configured to diagnose an anomaly in the component or system being monitored and can be operated by a user. In one embodiment, as shown in FIG. 2A, diagnostic device 230 is disposed on a rotorcraft 100. In another embodiment, as shown in FIG. 2B, at least a portion of the diagnostic device 230 is disposed on the rotorcraft and can be implemented by one or more computers across one or more networks.

One or more tachometers 210 may be used to detect rotational speed of a rotating component, e.g., a shaft, gear, and/or part of a bearing. Tachometer technologies include optical sensor based, hall sensor based, generator (e.g., coil sensor) based (including variable reluctance sensors) and other tachometer technologies known to those skilled in the art. A tachometer is configured to provide an output, e.g., a pulse, at a rate (e.g., pulses per revolution) that corresponds to (e.g., is proportional to) the rotational speed of the rotating component being monitored. In a preferred embodiment, the tachometer 210 is a variable reluctance sensor targeting a ferrous interrupter.

Figure 3A:
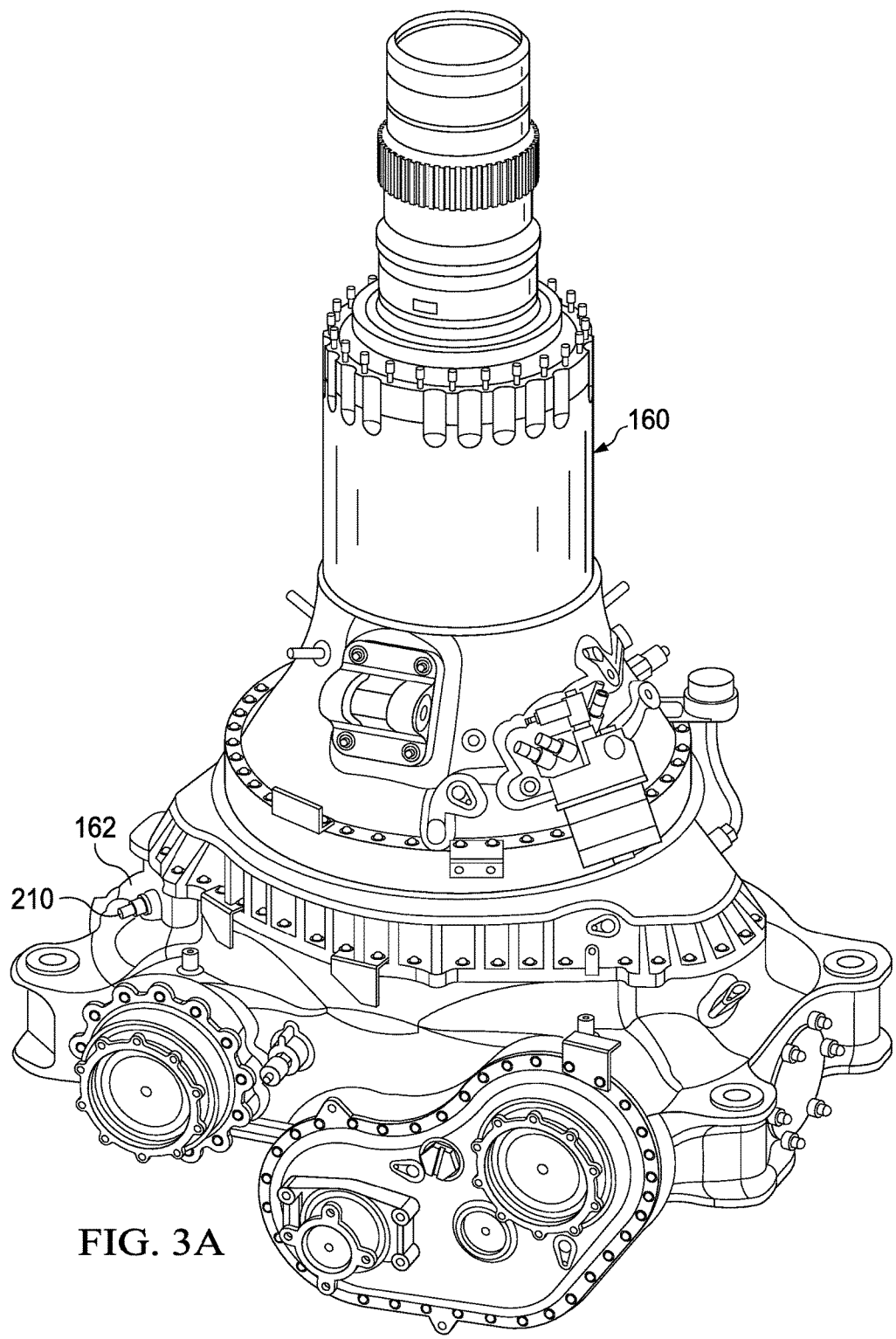
FIG. 3A is a perspective view of tachometer mounted to a gearbox in a drive train system; according to an illustrative embodiment.

In some embodiments, tachometer 210 can be mounted to a gearbox case 162 and monitor the rotational speed of a gear tooth passage. In the embodiment shown in FIG. 3A, the tachometer 210 is disposed adjacent to the left-hand input drive of gearbox 160 for detecting gear teeth passage of a bevel gear disposed therein.

Figure 3B:
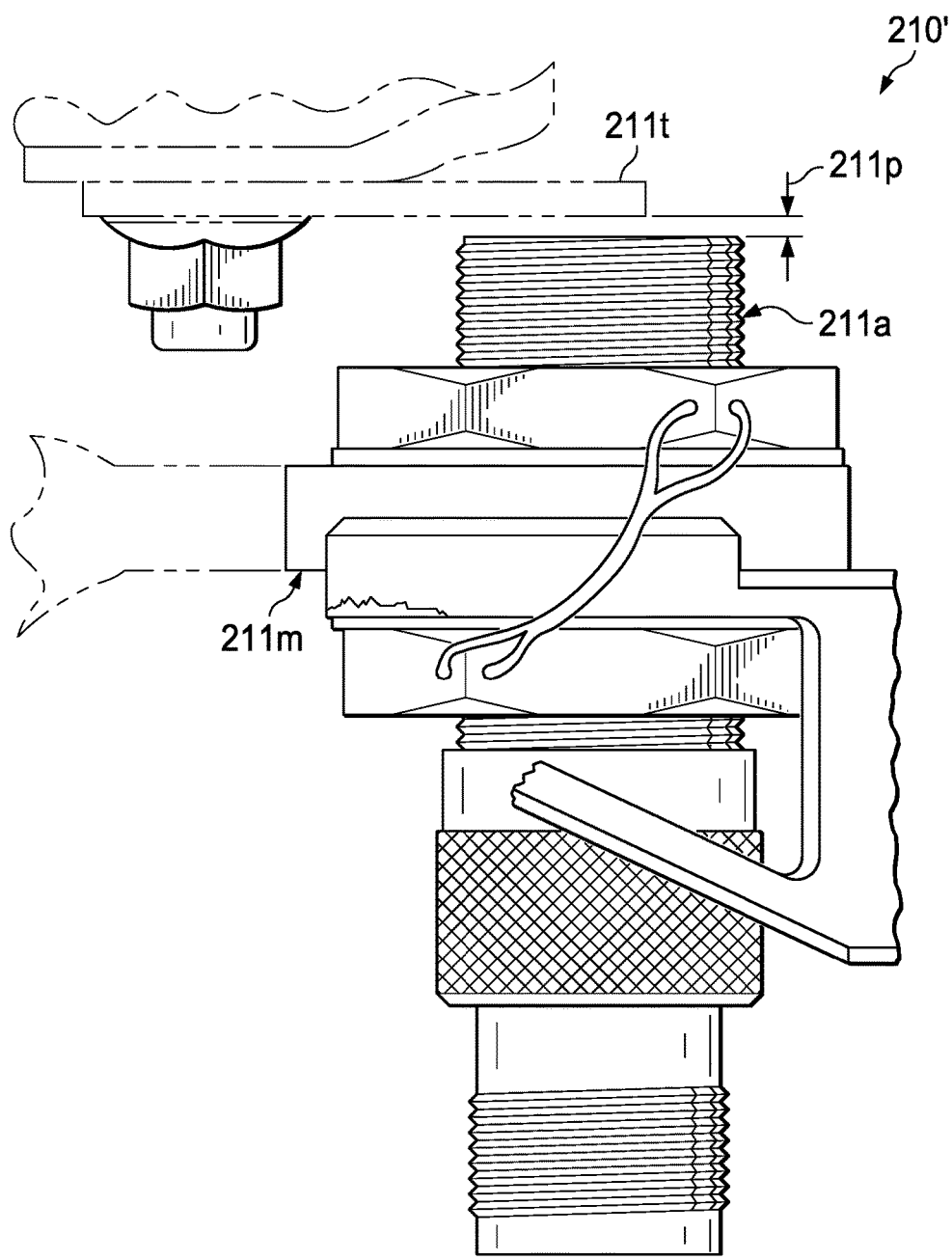
FIG. 3B is a schematic side view of a tachometer, according to an illustrative embodiment.

In another embodiment, shown in FIG. 3B, a tachometer 210' can be mounted adjacent to a shaft or other rotating component in gearbox 160. Tachometer 210' can include a tachometer body 211a mounted to a fixed portion of the gearbox 160 and an interrupter 211t mounted to a rotating shaft or other rotating component. An interrupter passage 211p is provided between the tachometer body 211a and the interrupter 211t. Tachometer body 211a can be coupled to the gearbox 160 by a tachometer mounting member 211m and secured thereon by a nut or other conventional fastener.

In an embodiment, only one tachometer 210 is located on a gearbox to monitor the health of the drive train 110. In an embodiment, at least two, three, four, five, six or more tachometers 210 are coupled to gearbox 160 to monitor the health of the monitored component or system. A further embodiment provides a plurality of tachometers to monitor the health of the drive train 110 and/or a component thereof.

One or more tachometers 210 can be disposed at one or more locations on drive train 110 to monitor the health of the drive system 110 or other rotational systems. A tachometer can be coupled to at least one of a gearbox, a bearing housing, a hanger bearing housing, a swashplate bearing housing, an engine, a transmission gearbox, engine gearbox, an oil blower, an oil cooler, a main rotor mast, a tail rotor drive shaft, a rotating component in drive train system, and a rotating system in a drive train system. Tachometer 210 can be disposed on, in, in a passage adjacent to, or, near the monitored component or system.

During operation, gearbox 160 transmits power from a power source (e.g., engine 112) to the object(s) to be moved (e.g., components in the drive train 110). Tachometer 210 is configured to detect the passage of its target (e.g., passage of gear teeth or other interrupters). Tachometer 210 can send an output of original data (e.g., the measurements of the passing target) to the diagnostic device 230. An illustrative embodiment, of original data from tachometer 210 is shown in FIG. 3C. The original data can be analyzed to determine a condition of a monitored component.

Figure 4A:
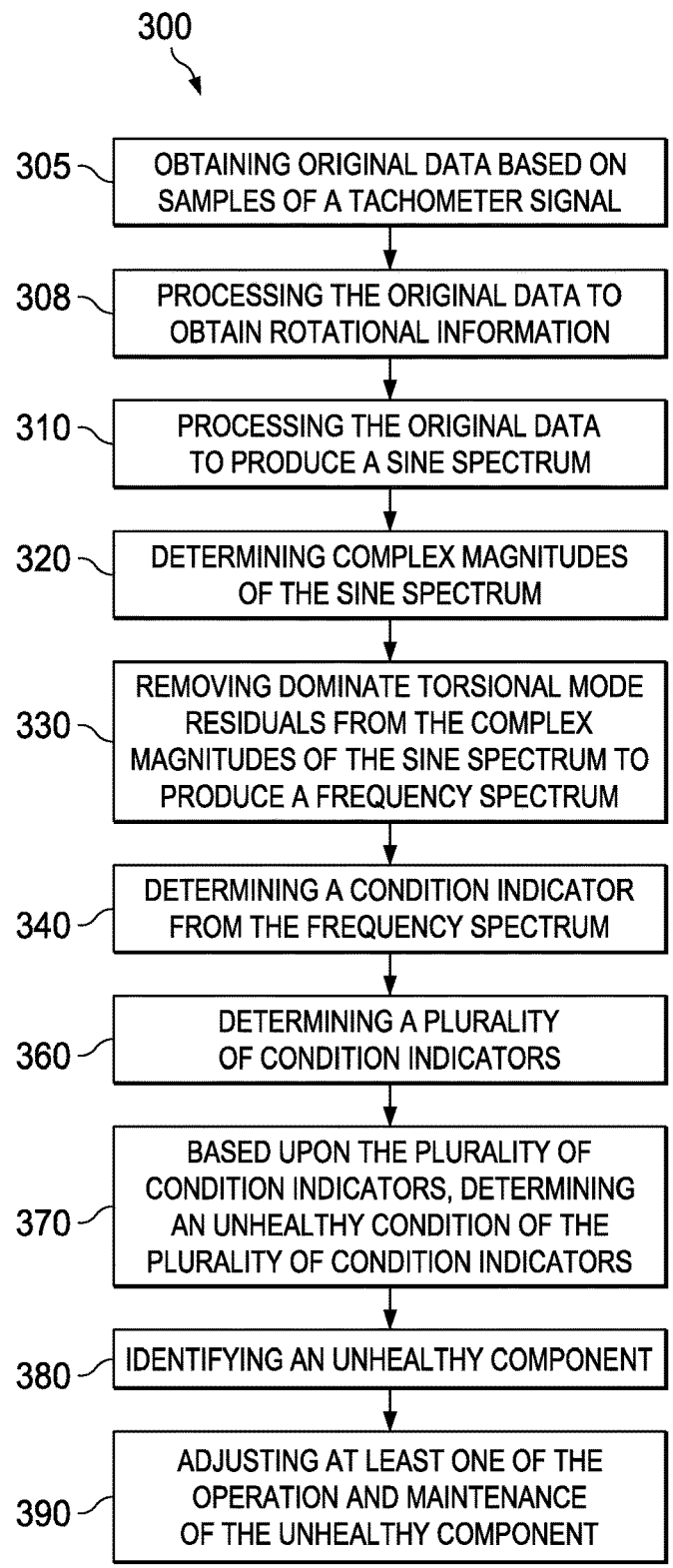
FIG. 4A is a flowchart showing an exemplary diagnostic method, according to an exemplary embodiment.
Figure 4B:
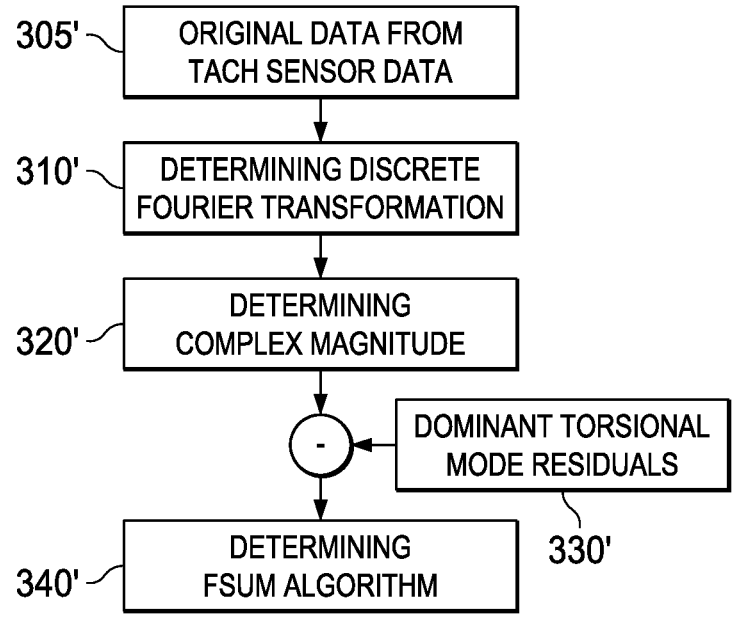
FIG. 4B is a flowchart showing an illustrative embodiment of a diagnostic method.

Diagnostic device 230 is configured to implement the method 300 of diagnosing an anomaly of a monitored component in a drive train 110. Method 300, as shown in FIG. 4, can include at least one or more of the following steps: a step 305 of obtaining original data based on samples of a tachometer signal; a step 308 of processing the original data to obtain rotational information; a step 310 of processing the original data to produce a sine spectrum; a step 320 of determining complex magnitudes of the sine spectrum; a step 330 of removing dominate torsional mode residuals from the complex magnitudes of the sine spectrum to produce a frequency spectrum; a step 340 of determining a condition indicator from the frequency spectrum; a step 360 of determining a plurality of condition indicators; a step 370 of determining an unhealthy condition based upon the plurality of condition indicators; a step 380 of identifying an unhealthy component; a step 390 of adjusting at least one of the operation and maintenance of the unhealthy component.

Method 300 can include the step 305 of obtaining original data based on samples of a tachometer signal. In an embodiment, diagnostic device 230 can select, or sample, at predetermined equal intervals of time measurements in the tachometer signal and digitize the tachometer signal to obtain a snapshot of original data. It should be appreciated that the sampling rate and method may be achieved using a wide variety of configurations; for example, the sampling rate can be modified for each different application (e.g., each different type of gearbox). Method 300 can include a step 308 of processing the original data to obtain rotational information.

The samples of the original data are then processed in step 310 to produce a sine spectrum. In an illustrative embodiment of the method 300, shown in FIG. 4B, where like features are identified by like numerals with a primed (') suffix, the processing of the original data is achieved by a discrete Fourier transform at step 310'. The complex magnitudes of the sine spectrum are then determined in step 320.

Step 330 includes removing dominate torsional mode residuals from the complex magnitudes of the sine spectrum to produce a frequency spectrum. In an embodiment, the step 330 of removing dominate torsional mode residuals includes removing dominate torsional frequency (DTF) of the drive system and harmonics of the DTF, as well as sidebands of the DTF and its harmonics from around the primary frequency of the tachometer signal and its harmonics. DTF is a characteristic of a particular gearbox operating in an aircraft, which cannot be obtained from a drive stand test. In an embodiment, the step of removing the dominate torsional mode residuals includes monitoring torsional vibrations of a gearbox in a drivetrain of a rotorcraft and identifying DTF of the gearbox, which indicates the dominate torsional mode residuals to be removed. In an embodiment, the step 330 of removing the dominate torsional mode residuals includes predetermining the highest frequency torsional mode of interest and zeroing all complex magnitudes within that frequency range around (and including) the primary frequency of the tachometer signal and its harmonics.

Figure 6:
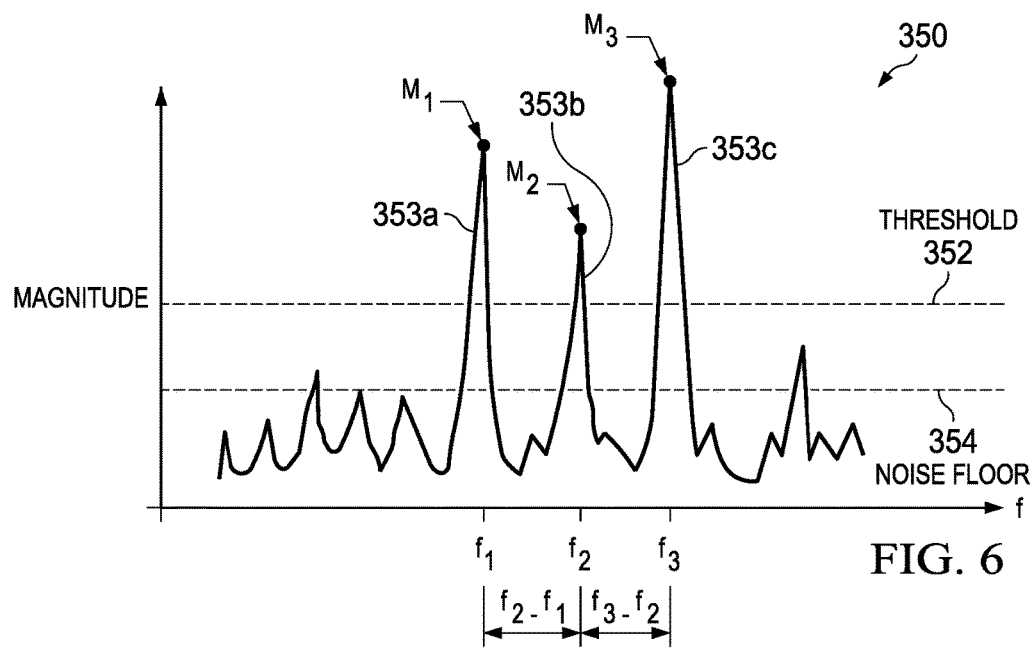
FIG. 6 is a prophetic example of a frequency spectrum illustrating the methods in FIG. 5, according to an exemplary embodiment.

Method 300 includes step 340 of determining a condition indicator based on the frequency spectrum. An exemplary frequency spectrum 350 is shown in FIG. 6. The X axis represents frequency. The Y axis represents the magnitude of the frequency spectrum 350. Frequency spectrum 350 includes spectral lines spaced apart at frequencies corresponding to the rotational speed of the component being assessed.

Figure 5:
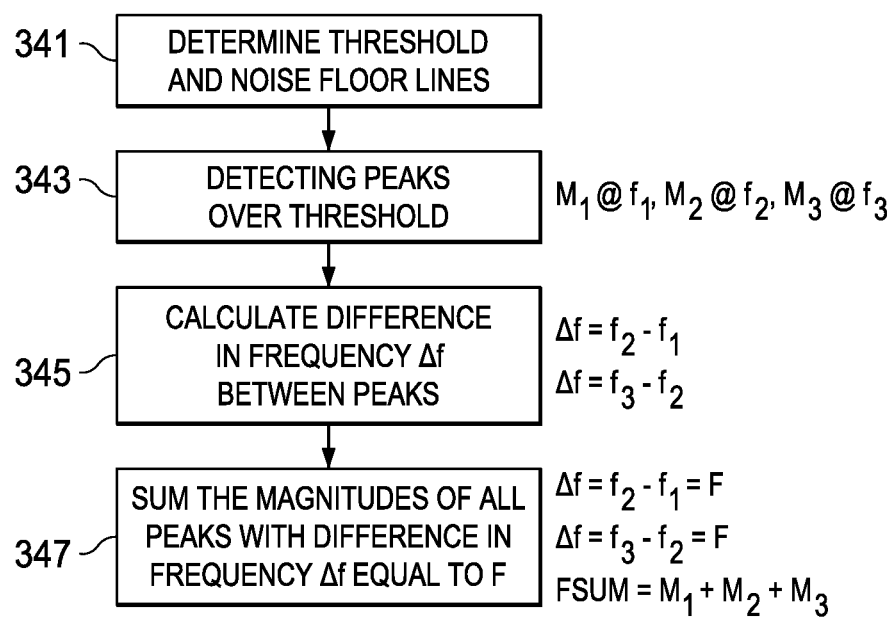
FIG. 5 is a flowchart illustrating a method for determining a condition indicator from a frequency spectrum, according to an exemplary embodiment.

The step 340 includes at least one or more of the steps identified in FIG. 5 including a step 341 of determining a threshold 352 and a noise floor 354. The threshold 352 is a line that is above the channel noise floor and below an upper limit. The threshold 352 and noise floor 354 can be determined after monitoring the tachometer data of a particular healthy gearbox over time (e.g., for a few snapshots per regime). In some embodiments, the threshold 352 and noise floor 354 can be predetermined if the digitizer resolution and other signal conditions are known. Both the threshold 352 and nose floor 354 remain at a constant level once determined for a particular tachometer channel, as shown in the illustrative embodiment shown in FIGS. 7A-7C.

Step 340 can include the following steps: a step 343 of detecting peaks over the threshold 352 (e.g., for the example shown in FIG. 6, peak 353a at frequency $f_1$ has a magnitude $M_1$, peak 353b at frequency $f_2$ has a magnitude $M_2$, peak 353c at frequency $f_3$ has a magnitude $M_3$); and a step 345 of calculating the difference in frequency $\Delta f$ between peaks (e.g., $\Delta f=f_2-f_1$; $\Delta f=f_3-f_2$); and a step 347 of summing the magnitudes of all peaks with difference in frequency equal to the rotational frequency F of the component or system (e.g., $M_1+M_2+M_{3-}$) which equals a condition indicator (FSUM).

Once a condition indicator has been determined, step 340 can be repeated to determine a plurality of condition indicators in step 360. Method 300 can include step 370 that is based upon the plurality of condition indicators, determining an unhealthy condition of the plurality of condition indicators. Step 370 can include displaying the plurality of condition indicators in a graphical representation and/or other methods for arranging a plurality of condition indicators.

Figure 8:
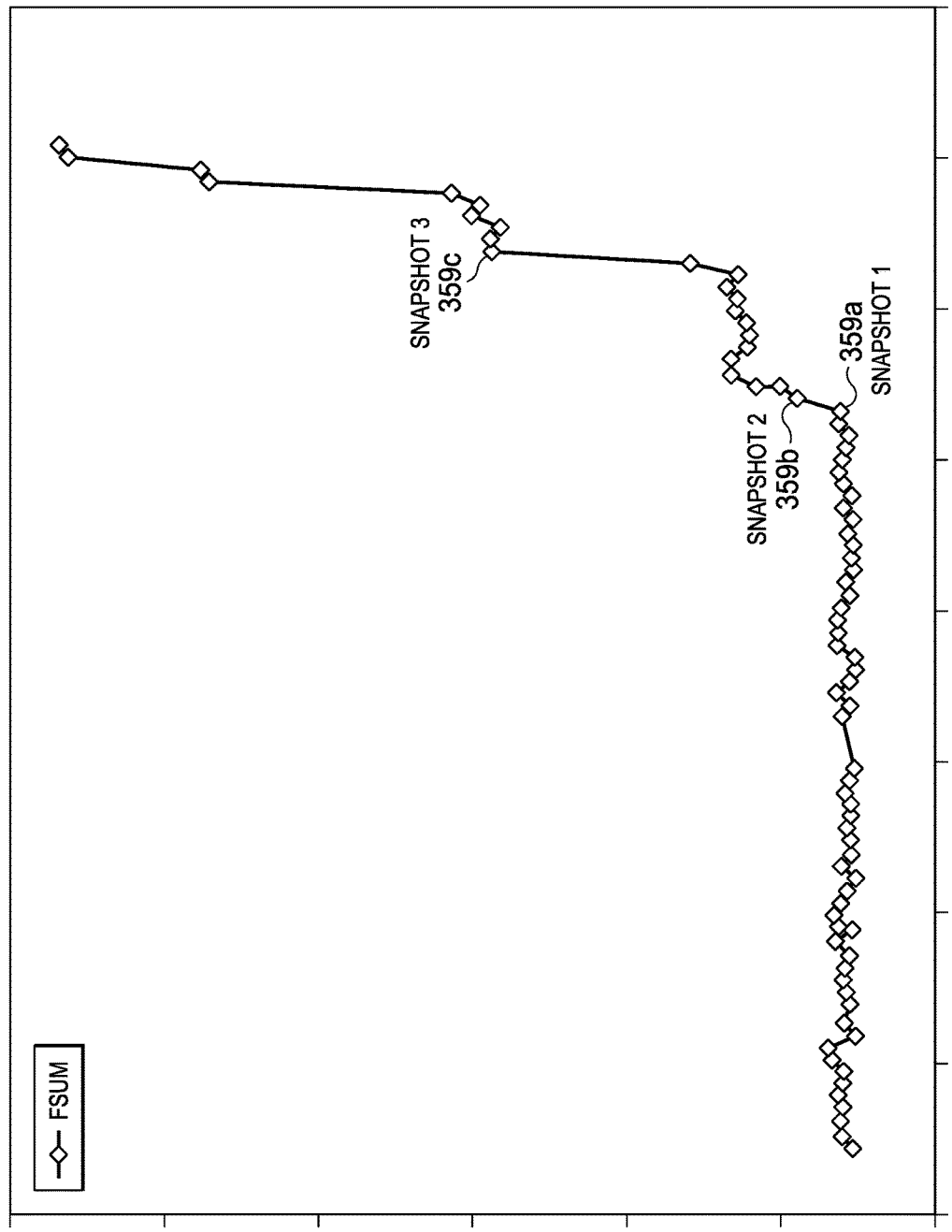
FIG. 8 is a graph illustrating a time history of the component degrading in FIGS. 7A-7C; according to an illustrative embodiment.

An illustrative embodiment of a plurality of condition indicators is shown in FIGS. 7A-7C and 8. FIGS. 7A-7C illustrate first, second, and third frequency spectrums 350a, 350b, 350c based on three successive snapshots of original data as a bull gear in a gearbox degrades over time. FIG. 7A includes a first frequency spectrum 350a with a plurality of peaks over the threshold line and a very few of these peaks spaced frequency F apart. The sum of the magnitudes of the peaks above the threshold line and spaced frequency F apart corresponds to first condition indicator 359a in FIG. 8. FIG. 7B includes a second frequency spectrum 350b with a greater number of peaks over the threshold line and more of these peaks spaced at frequency F apart, an example of two of these peaks spaced frequency F apart is depicted at 355b and 357b. The sum of the magnitudes of the peaks above the threshold line and spaced frequency F apart corresponds to second condition indicator 359b in FIG. 8. FIG. 7C includes a third frequency spectrum 350c with an even greater number of peaks over the threshold line and even more of these peaks spaced frequency F apart, an example of two of these peaks spaced frequency F apart is depicted at 355c and 357c. The sum of the magnitudes of the peaks above the threshold line and spaced frequency F apart corresponds to third condition indicator 359c in FIG. 8. As shown in FIG. 8, the first condition indicator 359a is within the healthy previous baseline condition indicators. Second and third condition indicators 359b, 359c increase in magnitude over the previous baseline condition indicators and the first condition indicator 359a. Second and third condition indicators 359b, 359c indicate an unhealthy condition of the monitored component.

Method 300 can include the step 380 of identifying an unhealthy component. In some embodiments, step 380 can also include identifying a particular type of defect. In some embodiments, the unhealthy component can include a plurality of unhealthy components. For example, the plurality of condition indicators can be used to identify a range of a healthy condition of the component being monitored. When the condition indicator increases above the range of the healthy condition, the condition indicator is in an unhealthy condition.

Method 300 can include the step 390 of adjusting at least one of the operation and maintenance of the unhealthy component. In an embodiment, the diagnostic device 230 analyzes the condition indicators, the identity of the unhealthy component, and/or the type of defect relating to the drive train 110 (health information) and identifies maintenance performed thereon. This analysis is done in order to assess the health of a particular monitored component and drive train 110. In an exemplary embodiment, the diagnostic device 230 may determine, based on the health information, that a monitored component is nearing failure, and generate an indication that the component requires maintenance. In an embodiment, the maintenance of an unhealthy component can be adjusted by determining when the unhealthy component should be repaired and/or replaced. An indication could be presented on a display, printed out on a hard copy, or may take the form of an automatically generated work order that identifies a necessary maintenance task for the drive train 110. In a particular embodiment, once the unhealthy component is identified, step 390 can include the pilot, crew, or other user remote from the aircraft adjusting the aircraft speed or other operational parameters to reduce, disengage or otherwise lessen the impact of the unhealthy component in the drive train 110 from damage and/or to reduce the likelihood of catastrophic failure during flight. In some embodiments, method 300 may predict upcoming replacement and/or repair times of an unhealthy component to ensure that the component is not replaced and/or repaired prematurely. Since the unhealthy component can be identified prior to failure using the systems, methods and devices described herein, the unhealthy component can advantageously be repaired or replaced prior to damaging other components in the drive train 110.

Diagnostic system 200 may be installed on-board an aircraft 100 (as indicated in FIG. 2A), off-board (such as at a ground facility), or a combination of the two (as indicated in FIG. 2B). In an exemplary embodiment, when diagnostic system 200 is installed on-board aircraft 200, diagnostic system 200 can include a member 232 and a processor 234. In an embodiment, memory 232 is configured to store the output of original data indicative of the vibration, sounds, and/or acoustic signals over time. In an embodiment, the output of original data is stored in memory 232 at least before the diagnostic method 300 is initiated. Memory 232 represents any suitable storage mechanism and may store any data for use by a computer system. Memory 232 may comprise one or more tangible, computer-readable, and/or computer-executable storage medium. Examples of memory 232 include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable medium. In an embodiment, processor 234 is configured to process original data from the tachometer 210 and/or memory 232.

Diagnostic system 200 can include or otherwise be operably associated with a health and usage monitoring system (HUMS) 250 and a display 260. In an embodiment, HUMS 250 can receive outputs from the processor 234 regarding the health condition of the monitored component or system. In one embodiment, display 260 can receive outputs from the processor 234 that provide a visual indication of real-time health condition of the monitored component or system. Accordingly, a pilot of the rotorcraft 100 can be alerted to the real-time health condition of the monitored component in the drive train 110.

In another embodiment, as shown in FIG. 2B, diagnostic system 200 can be implemented by one or more computer systems 236 across one or more networks 238 and accessible by a user 240. Diagnostic system 200, as shown in FIG. 2B, can be configured to store original data related to the monitored component or system in memory 232. In an embodiment, the output of original data is stored in memory 232 at least before the original data is transmitted to one or more computers 236. The original data obtained by tachometer 210 is transferred to one or more computer systems 236, typically after each flight. Computers systems 236 can be fixed or mobile on a ground station at various locations (e.g., an airport, military base, command center, manufacturer). The original data can be transferred over network 238 and/or using physical cabling or media; for example, but not limited to, hardwire cabling such as parallel cables, serial cables, USB cables, Firewire cables or the like or wireless protocols such as Bluetooth connectivity, infrared connectivity, radio transmission connectivity, Wi-Fi connectivity, other suitable communications protocol, removable memory cards, flash memory mass device, solid-state floppy disk card, non-volatile memory card, or other suitable memory storage entity.

Figure 9:
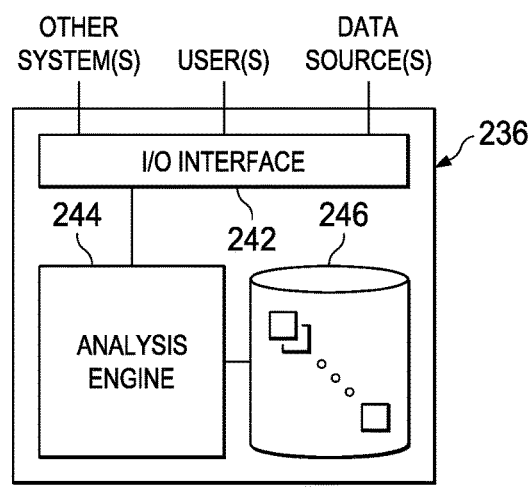
FIG. 9 is a schematic block diagram of a computer system, according to an illustrative embodiment.

Diagnostic system 230 can include computer system 236 as shown on FIG. 9. Computer system 236 can include an input/output (I/O) interface 242, an analysis engine 244, and a database 246. Alternative embodiments can combine or distribute the input/output (I/O) interface 242, analysis engine 244, and database 246, as desired.

Embodiments of system 236 can include one or more computers that include one or more processors and memories configured for performing tasks described herein. This can include, for example, a computer having a central processing unit (CPU) and non-volatile memory that stores software instructions for instructing the CPU to perform at least some of the tasks described herein. This can also include, for example, two or more computers that are in communication via a computer network, where one or more of the computers include a CPU and non-volatile memory, and one or more of the computer's non-volatile memory stores software instructions for instructing any of the CPU(s) to perform any of the tasks described herein. Thus, while the exemplary embodiment is described in terms of a discrete machine, it should be appreciated that this description is non-limiting, and that the present description applies equally to numerous other arrangements involving one or more machines performing tasks distributed in any way among the one or more machines. It should also be appreciated that such machines need not be dedicated to performing tasks described herein, but instead can be multi-purpose machines, for example computer workstations, that are suitable for also performing other tasks.

The I/O interface 242 can provide a communication link between external users, systems, and data sources and components of the system 236. The I/O interface 242 can be configured for allowing one or more users 240 to input information to the system 236 via any known input device. Examples can include tachometer 210, memory 232, a keyboard, mouse, touch screen, and/or any other desired input device. The I/O interface 242 can be configured for allowing one or more users to receive information output from the system 236 via any known output device. Examples can include a display monitor, a printer, and/or any other desired output device. The I/O interface 242 can be configured for allowing other systems to communicate with the system 236. For example, the I/O interface 242 can allow one or more remote computer(s) to access information, input information, and/or remotely instruct the system 236 to perform one or more of the tasks described herein. The I/O interface 242 can be configured for allowing communication with one or more remote data sources.

For example, the I/O interface 242 can allow one or more remote data source(s) to access information, input information, and/or remotely instruct the system 236 to perform one or more of the tasks described herein.

The database 246 provides persistent data storage for system 236. While the term "database" is primarily used, a memory or other suitable data storage arrangement may provide the functionality of the database 246. In alternative embodiments, the database 246 can be integral to or separate from the system 236 and can operate on one or more computers. The database 246 preferably provides non-volatile data storage for any information suitable to support the operation of the system 236, including various types of data discussed further herein.

The analysis engine 244 can be configured for implementing at least one step in method 300. The analysis engine 244 can include various combinations of one or more processors, memories, and software components.

The device, system, and methods described herein can advantageously provide at least one of the following benefits: (1) the capability to collect and record rotational information about aircraft components and systems during operation; (2) the capability to determine which component in the drive train is failing using only a tachometer; (3) determine when a component in the drive train should be replaced or repaired prior to failure, which can prevent further damage to adjacent components; (4) only requires a tachometer (and does not use an accelerometer or other type of vibration sensor); and (5) the ability to adjust the operation of the aircraft to lessen the impact of the unhealthy component in the drive train on the safety of the flight and damage to other components in the drive train.

The particular embodiments disclosed above are illustrative only, as the apparatus may be modified and practiced in different but equivalent manners apparent to those skilled in the art having the benefit of teachings herein. Modifications, additions, or omissions may be made to the apparatuses described herein without departing from the scope of the invention. The components of the apparatus may be integrated or separated. Moreover, the operations of the apparatus may be performed by more, fewer, or other components.

It may be advantageous to set forth definitions of certain words and phrases used in this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The terms "a" and "an" are defined as one or more unless this disclosure explicitly requires otherwise.

Furthermore, no limitations are intended to the details of construction or design herein shown, other than as described in the claims below. It is therefore evident that the particular embodiments disclosed above may be altered or modified and all such variations are considered within the scope and spirit of the application. Accordingly, the protection sought herein is as set forth in the claims below.

What is claimed is:

1. A method of diagnosing an anomaly of a monitored component in a drive train, the method comprising:
    obtaining, by a device configured to diagnose an anomaly, original data based only on samples of a tachometer signal;
    processing, by the device configured to diagnose the anomaly, the original data to obtain rotational information;
    processing, by the device configured to diagnose the anomaly, the original data to produce a sine spectrum;
    determining, by the device configured to diagnose the anomaly, complex magnitudes of the sine spectrum;
    removing, by the device configured to diagnose the anomaly, dominate torsional mode residuals from the complex magnitudes of the sine spectrum to produce a frequency spectrum; and
    determining, by the device configured to diagnose the anomaly, a condition indicator from the frequency spectrum;
    wherein the step of determining the condition indicator from the frequency spectrum comprises:
    (a) determining a threshold and a noise floor for the frequency spectrum;
    (b) detecting peaks of the frequency spectrum over the threshold, each peak having a frequency and a magnitude;
    (c) calculating the difference in the frequency between the peaks; and
    (d) summing the magnitudes of all peaks with a difference in the frequency equal to a rotational frequency of the component to determine the condition indicator.

2. The method according to claim 1, wherein the step of processing to produce the sine spectrum comprises performing a discrete Fourier transform (DFT).

3. The method according to claim 1, wherein the step of removing dominate torsional mode residuals comprises:
    monitoring torsional vibrations in a gearbox in a drivetrain of a rotorcraft; and
    identifying the dominate torsional mode residuals of the gearbox.

4. The method according to claim 1, further comprising: determining a plurality of condition indicators.

5. The method according to claim 4, further comprising:
    based upon the plurality of condition indicators, determining an unhealthy condition of the plurality of condition indicators.

6. The method according to claim 5, further comprising: identifying an unhealthy component.

7. The method according to claim 6, further comprising: adjusting at least one of an operation and a maintenance of the unhealthy component.

8. The method according to claim 1, wherein the device configured to diagnose the anomaly further comprises:
    a display;
    wherein the device provides a real-time indication of the anomaly in the monitored component.

9. The method according to claim 1, further comprising:
    storing a history, by the device configured to diagnose the anomaly, of original data;
    wherein the history being stored before a diagnostic operation for the component is performed.

10. A device configured to diagnose an anomaly of a monitored component in a drive train, the device comprising:
    a memory configured to store original data of a tachometer signal;
    one or more processors in communication with the memory, the one or more processors being configured to:
        obtain a original data based only on samples of the tachometer signal;
        process the original data to obtain rotational information;
        process the original data to produce a sine spectrum;
        determine complex magnitudes of the sine spectrum;
        remove dominate torsional mode residuals from the complex magnitudes of the sine spectrum to produce a frequency spectrum; and
        determine a condition indicator from the frequency spectrum;
    wherein the determine the condition indicator from the frequency spectrum comprises:
    (a) determine a threshold and a noise floor for the frequency spectrum;
    (b) detect peaks of the frequency spectrum over the threshold, each peak having a frequency and a magnitude;
    (c) calculate the difference in the frequency between the peaks; and
    (d) sum the magnitudes of all peaks with a difference in the frequency equal to a rotational frequency of the component to determine the condition indicator.

11. The device according to claim 10, wherein the processors are configured to:
    determine a plurality of condition indicators.

12. The device according to claim 11, wherein the processors are configured to:
    based upon the plurality of condition indicators, determine an unhealthy condition of the plurality of condition indicators; and
    identify an unhealthy component.

13. The device according to claim 12, wherein the processors are configured to:
    adjust at least one of an operation and a maintenance of the unhealthy component.

14. The device according to claim 10, wherein the device further comprises:
    a display;
    wherein the device provides a real-time indication of the anomaly in the monitored component.

15. The device according to claim 10, wherein the original data is stored before a diagnostic operation for the component is performed.

16. A system for diagnosing an anomaly of a monitored component in a drive train, the system comprising:
- a rotorcraft comprising a body, a power train coupled to the body and comprising a power source and a drive train coupled to the power source;
- a tachometer coupled to the drive train; and
- a diagnostic device associated with the tachometer, the diagnostic device operable to:
  - obtain original data based only on samples of a tachometer signal;
  - process the original data to obtain rotational information;
  - process the original data to produce a sine spectrum;
  - determine complex magnitudes of the sine spectrum;
  - remove dominate torsional mode residuals from the complex magnitudes of the sine spectrum to produce a frequency spectrum; and
  - determine a condition indicator from the frequency spectrum;
- wherein the determine the condition indicator from the frequency spectrum comprises:
  - (a) determine a threshold and a noise floor for the frequency spectrum;
  - (b) detect peaks of the frequency spectrum over the threshold, each peak having a frequency and a magnitude;
  - (c) calculate the difference in the frequency between the peaks; and
  - (d) sum the magnitudes of all peaks with a difference in the frequency equal to a rotational frequency of the component to determine the condition indicator.

17. A non-transitory computer-readable storage medium encoded with instructions that, when executed, cause one or more processors of a computing device to diagnose an anomaly of a monitored component in a drive train to:
- obtain original data based only on samples of a tachometer signal;
- process the original data to obtain rotational information;
- process the original data to produce a sine spectrum;
- determine complex magnitudes of the sine spectrum;
- remove dominate torsional mode residuals from the complex magnitudes of the sine spectrum to produce a frequency spectrum; and
- determine a condition indicator from the frequency spectrum;
- wherein the determine the condition indicator from the frequency spectrum comprises:
  - (a) determine a threshold and a noise floor for the frequency spectrum;
  - (b) detect peaks of the frequency spectrum over the threshold, each peak having a frequency and a magnitude;
  - (c) calculate the difference in the frequency between the peaks; and
  - (d) sum the magnitudes of all peaks with a difference in the frequency equal to a rotational frequency of the component to determine the condition indicator.

* * * * *